United States Patent
Grant (10) Patent No.: US 11,353,960 B1
(45) Date of Patent: Jun. 7, 2022

(54) INTRAOCULAR BRAIN INTERFACE

(71) Applicant: Strathspey Crown, LLC, Newport Beach, CA (US)

(72) Inventor: Robert Edward Grant, Laguna Beach, CA (US)

(73) Assignee: Strathspey Crown, LLC, Newport Beach, CA (US)

( * ) Notice: Subject to any disclaimer, the term of this patent is extended or adjusted under 35 U.S.C. 154(b) by 7 days.

(21) Appl. No.: 17/103,571

(22) Filed: Nov. 24, 2020

(51) Int. Cl.
*G06F 3/01* (2006.01)
*G06T 19/00* (2011.01)
*A61F 2/14* (2006.01)

(52) U.S. Cl.
CPC ................ *G06F 3/015* (2013.01); *A61F 2/14* (2013.01); *G06T 19/006* (2013.01)

(58) Field of Classification Search
None
See application file for complete search history.

(56) References Cited

U.S. PATENT DOCUMENTS

| | | | |
|---|---|---|---|
| 7,001,427 B2 * | 2/2006 | Aharoni | A61N 1/36046 623/4.1 |
| 7,144,423 B2 | 12/2006 | McDonald | |
| 7,229,475 B2 | 6/2007 | Glazier | |
| 8,608,310 B2 | 12/2013 | Otis | |
| 8,778,022 B2 | 7/2014 | Blum | |
| 9,101,279 B2 * | 8/2015 | Ritchey | A61B 5/1114 |
| 9,302,103 B1 | 4/2016 | Nirenberg | |
| 9,662,199 B2 | 5/2017 | Grant | |
| 9,995,936 B1 | 6/2018 | Macannuco | |
| 10,052,196 B2 | 8/2018 | Pugh | |
| 10,123,869 B2 * | 11/2018 | Blanckaert | A61B 5/1107 |
| 10,126,569 B2 | 11/2018 | Blum | |
| 10,144,707 B2 | 12/2018 | Russo | |
| 10,299,912 B2 | 5/2019 | Grant | |
| 10,447,966 B2 | 10/2019 | Ritchey | |
| 10,467,992 B2 | 11/2019 | Deering | |
| 11,118,172 B2 * | 9/2021 | Grant | A61B 5/053 |
| 11,182,124 B1 * | 11/2021 | Ray | G02B 27/0172 |
| 11,200,241 B2 * | 12/2021 | Delaney | G06F 16/243 |
| 2006/0049957 A1 | 3/2006 | Surgenor | |
| 2006/0149338 A1 | 7/2006 | Flaherty | |
| 2010/0234942 A1 | 9/2010 | Peyman | |
| 2013/0044042 A1 | 2/2013 | Olsson | |
| 2013/0063550 A1 * | 3/2013 | Ritchey | G06F 3/015 348/36 |

(Continued)

FOREIGN PATENT DOCUMENTS

| | | |
|---|---|---|
| CN | 110767036 | 2/2020 |
| EP | 2593040 | 3/2016 |

(Continued)

OTHER PUBLICATIONS

Mercier-Ganady, Jonathan, et al. "The Mind-Mirror: See your brain in action in your head using EEG and augmented reality." 2014 IEEE Virtual Reality (VR). IEEE, 2014.*

(Continued)

*Primary Examiner* — Ryan M Gray
(74) *Attorney, Agent, or Firm* — Fish IP Law, LLP (57) ABSTRACT

An intraocular brain interface system that detects a user's neuronal activity and uses it to identify an image associated with that neuronal activity. Once identified, the image is presented to the user via an intraocular display component such that only the user is able to see the image.

10 Claims, 4 Drawing Sheets

(56) References Cited

U.S. PATENT DOCUMENTS

| | | | |
|---|---|---|---|
| 2013/0194540 A1 | 8/2013 | Pugh | |
| 2015/0036221 A1 | 2/2015 | Stephenson | |
| 2017/0042713 A1* | 2/2017 | Nurmikko | A61B 5/145 |
| 2017/0075414 A1* | 3/2017 | Grant | G06F 3/011 |
| 2017/0270636 A1 | 9/2017 | Shtukater | |
| 2018/0153429 A1 | 6/2018 | Hua | |
| 2019/0332168 A1* | 10/2019 | Weldemariam | A61B 3/112 |
| 2020/0139077 A1 | 5/2020 | Biradar | |
| 2020/0205735 A1 | 7/2020 | Narayanan | |
| 2021/0023273 A1* | 1/2021 | Ben M'Barek | A61L 27/3813 |
| 2021/0348991 A1* | 11/2021 | Chung | G01N 1/30 |

FOREIGN PATENT DOCUMENTS

| | | |
|---|---|---|
| KR | 101895085 | 10/2018 |
| WO | 2006015315 | 2/2006 |

OTHER PUBLICATIONS

Messer, A'ndrea Elyse. "Your brain with a migraine: Effect of electric currents," Penn State. Jun. 27, 2018. 5 pages.

Milikovsky, Dan Z.; et al. "Electrocorticographic Dynamics as a Novel Biomarker in Five Models of Epileptogenesis," The Journal of Neuroscience, Apr. 26, 2017. 12 pages.

"Electroencephalogram (EEG)," Mayfield Brain & Spine, www.mayfieldclinic.com. Apr. 2018. 2 pages.

Li, Ting-Mei; et al. "Emotion classification based on brain wave: a survey," Hum. Cent. Comput. Inf. Sci. (2019) 9:42. 17 pages.

Liu, Ning-Han; et al. "Improving Driver Alertness through Music Selection Using a Mobile EEG to Detect Brainwaves," www.mdpi.com/journal/sensors. 2013. 23 pages.

International search report dated Mar. 18, 2022, for related PCT application No. PCT/US21/60835. 8 pages.

\* cited by examiner

INTRAOCULAR BRAIN INTERFACE

FIELD OF THE INVENTION

The field of the invention is implantable brain interfaces.

BACKGROUND

The background description includes information that may be useful in understanding the present invention. It is not an admission that any of the information provided herein is prior art or relevant to the presently claimed invention, or that any publication specifically or implicitly referenced is prior art.

Implantable devices have created new ways of enhancing the human experience. For example, implantable cameras have made it possible to enhance a person's visual abilities. Implantable sensors have enabled rapid detection of detrimental conditions within the body, allowing for earlier diagnosis and treatment.

However, existing implant technologies have yet to be leveraged to assist users with memory and recollection functions, such as to enhance these functions or to help users overcome deterioration in these functions. Thus, there is still a need for implantable systems that enhance memory and recollection in the user.

SUMMARY OF THE INVENTION

The inventive subject matter provides apparatus, systems and methods in which a visualization system enables the visualization of neural activity of a person. The systems and methods of the inventive subject matter include a detecting electronics component that detects neuronal emissions. In most embodiments, the neuronal emissions are emitted by the brain of a person (i.e., the user) wearing the visualization system.

The systems and methods of the inventive subject matter also include an analytics electronics component that associates the neuronal emissions with an image. In response to this association, the systems and methods of the inventive subject matter render the image, at least a portion of the image, or an image associated with the image on a display implanted within the eye of the user.

The image rendered can be a still image or a moving image and can be a photograph, video sequence, or an entirely computer-generated image.

In some embodiments, the detecting electronics component is positioned somewhere within the head of the user. For example, in embodiments, the detecting electronics component is implanted subdermally in the head of the user. In other embodiments, the detecting electronics component is positioned within the eye of the user.

In other embodiments, the detecting electronics component is positioned elsewhere in the user's body. In some of these embodiments, the detecting electronics is positioned over a portion of the user's spine. In other embodiments, the detecting electronics component is positioned over a portion of the peripheral nervous system of the user.

In embodiments, a second user can also have a second one or more of the components of the system implanted. In these embodiments, an image obtained based on the neuronal emissions of a first user can be transmitted to and displayed for a second user.

Various objects, features, aspects and advantages of the inventive subject matter will become more apparent from the following detailed description of preferred embodiments, along with the accompanying drawing figures in which like numerals represent like components.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

The following description includes information that may be useful in understanding the present invention. It is not an admission that any of the information provided herein is prior art or relevant to the presently claimed invention, or that any publication specifically or implicitly referenced is prior art.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of

DETAILED DESCRIPTION

Throughout the following discussion, numerous references will be made regarding servers, services, interfaces, engines, modules, clients, peers, portals, platforms, or other systems formed from computing devices. It should be appreciated that the use of such terms, is deemed to represent one or more computing devices having at least one processor (e.g., ASIC, FPGA, DSP, x86, ARM, ColdFire, GPU, multi-core processors, etc.) programmed to execute software instructions stored on a computer readable tangible, non-transitory medium (e.g., hard drive, solid state drive, RAM, flash, ROM, etc.). For example, a server can include one or more computers operating as a web server, database server, or other type of computer server in a manner to fulfill described roles, responsibilities, or functions. One should further appreciate the disclosed computer-based algorithms, processes, methods, or other types of instruction sets can be embodied as a computer program product comprising a non-transitory, tangible computer readable media storing the instructions that cause a processor to execute the disclosed steps. The various servers, systems, databases, or interfaces can exchange data using standardized protocols or algorithms, possibly based on HTTP, HTTPS, AES, public-private key exchanges, web service APIs, known financial transaction protocols, or other electronic information exchanging methods. Data exchanges can be conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Figure 1:
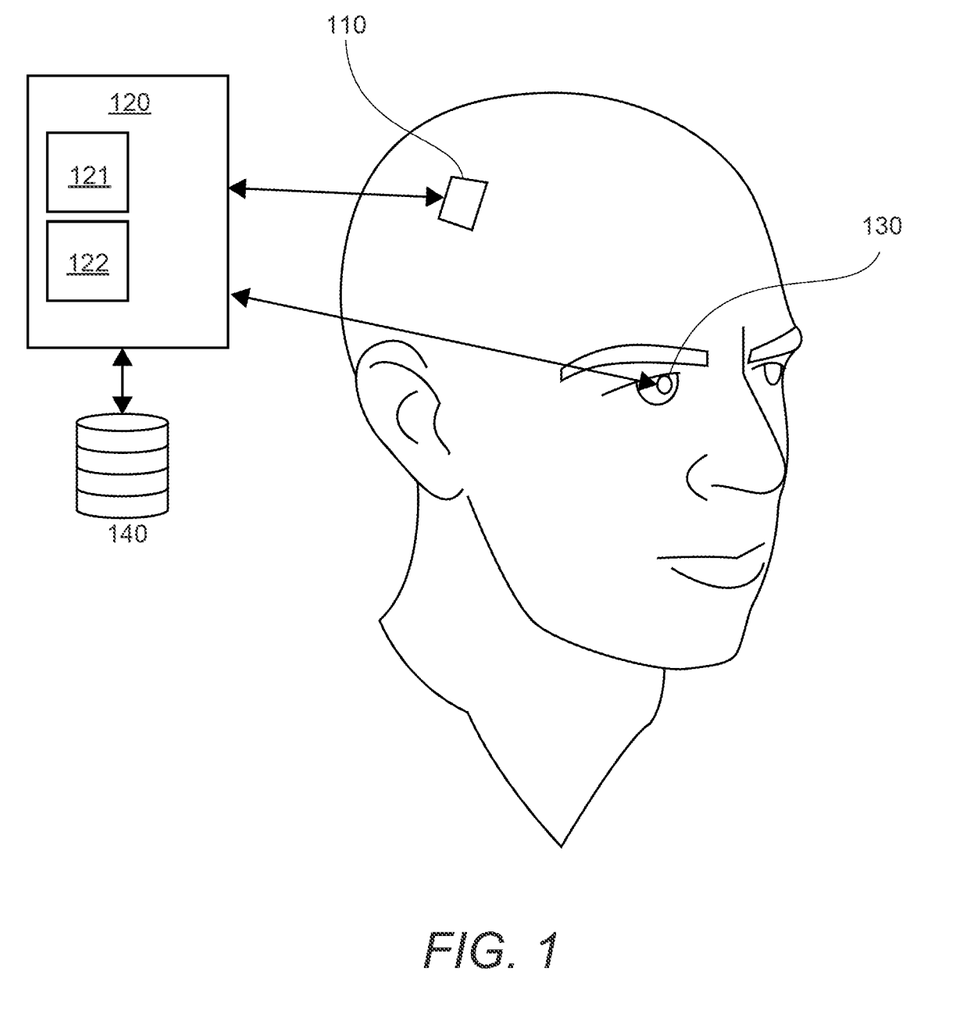
FIG. 1 is a diagrammatic overview of a system according to embodiments of the inventive subject matter.

FIG. 1 provides a diagrammatic overview of a system 100 according to embodiments of the inventive subject matter.

As seen in FIG. 1, the system 100 includes a detecting electronic component 110, an analytics electronics component 120 and a display component 130.

The detecting electronics component 110 is a hardware component that includes a sensor capable of detecting neuronal emissions. Neuronal emissions are detectable signals (e.g., neural oscillations, or brainwaves) emitted from neuronal activity in the brain of the user. As used herein, the terms "neuronal emissions", "neuronal oscillations" or "brainwaves" include, but are not limited to, waves typically grouped according to predominant frequencies, Delta (0.5 TO 3 Hz), Theta (3 TO 8 HZ), Alpha (8 TO 12 HZ), Beta (12 TO 38 HZ), or Gamma (38 TO 42 HZ) waves.

Conditions other than drowsiness can also be detected using brainwaves. For example, brainwaves can be used to detect dizziness and nausea ("Electroencephalogram (EEG), Mayfield Clinic, April, 2018"), as well as migraine-auras ("Your brain with a migraine effect of electric currents, ScienceDaily, Jun. 27, 2018"). Brainwaves can even be used to detect physical motions of a person (Emotion classification based on brain wave: a survey, Li et al., Hum. Cent. Comput. Inf. Sci., 2019"). Still further, brainwaves can be used to detect aura of epilepsy (Dan Z. Milikovsky et al, "Electrocorticographic Dynamics as a Novel Biomarker in Five Models of Epileptogenesis", The Journal of Neuroscience, 2017; 37 (17): 4450 DOI: 10.1523/JNEUROSCI.2446-16.2017).

The detecting electronics component 110 includes a data exchange interface that enables it to be communicatively coupled with the analytics electronics component 120 so as to transmit the neural emissions signals to the analytics electronics component 120. The data exchange interface can be one or more wireless and/or wired data exchange interfaces.

In embodiments of the inventive subject matter, the detecting electronics component 110 is a cranial implant positioned in the head of the user. As used herein, the term "cranial implant" means a sensor positioned somewhere on the head of a person. Cranial implants can be located supra- or sub-dermal, or within the cranium, or extend across one or more of those domains Some of the critical components are known in the prior art, but not for the claimed methods. US2018/0153429A1 to Hua describes cranial implants that can be used to monitor brainwaves, including those associated with epilepsy.

In embodiments of the inventive subject matter, the detecting electronics component 110 can be implanted within the eye of the user. In a variation of these embodiments, the detecting electronics component 110 and the display electronics component 130 can be integral to the same device.

In embodiments of the inventive subject matter, the detecting electronics component 110 is an implanted sensor that is positioned over a portion of the spine of the person.

In embodiments, the detecting electronics component is an implanted sensor positioned over a portion of the peripheral nervous system of the user.

The analytics electronics component 120 includes a processor 121 that enable it to carry out its associated processes and a non-transitory computer readable storage medium 122 (e.g., hard drive, RAM, etc.) that store the processor-executable instructions associated with the processes of the inventive subject matter. The analytics electronics component 120 also includes data communication interfaces such that it is capable of exchanging data with other system components and other computing devices. The data communication interfaces are preferably wireless communication interfaces (e.g., Wi-Fi, cellular, NFC, Bluetooth, or other wireless protocol). However, in certain embodiments where the analytics electronics component 120 is in close proximity to the detecting electronics component 110 and/or display electronics component 130, it is contemplated that the data communication can be wired or otherwise physically coupled (e.g., embodiments where one or more of the components 110, 120, 130 are within the same device). As such, the analytics electronics component 120 is communicatively coupled with the detecting electronics component 110 and the display component 130 such that it can receive data communications from the detecting electronics component 110 and transmit data to the display component 130.

The analytics electronics component 120 includes a non-transitory computer-readable memory that store the computer-executable instructions carried out by its processor to perform the steps associated with the inventive subject matter.

In embodiments of the inventive subject matter, the analytics electronics component 120 is implanted in the body of the user.

In other embodiments of the inventive subject matter, the analytics electronics component 120 is a computing device external to the user's body. In these embodiments, the analytics electronic component 120 includes a wireless communication interface sufficiently powerful to be able to communicate with the detecting electronics component 110 and the display component 130.

The display component 130 is a hardware component that can be implanted into the eye of the user. The display component 130 includes a display that can display an image within the eye such it is visible to the user.

U.S. Pat. Nos. 9,662,199 and 10,299,912, both to Robert Grant, describe an intra-optic lens having electronics for receiving and transmitting data, a digital display, a processor, memory, and an inductively charged power source. US patent application 2017/0075414, also to Grant, describes an implantable/wearable device for detecting diverse anatomical/physiological data. WO 2006/015315 to Feldon describes a digital display positioned on an intraocular lens. US 2013/0194540 to Pugh describes antennas and antenna systems configured into ophthalmic devices, including contact lenses. US 2010/0234942A1 (Peyman) describes intraocular lenses having pigment that can be adjusted automatically by the intensity of the external light, or by electrical stimulation. U.S. Pat. No. 7,001,427 to Aharoni, et al also discusses an intraocular display. All of these references are incorporated by reference in their entirety.

In one or more of the detecting electronics component 110, analytics electronics component 120 and display component 130 includes a battery that powers the corresponding electronics component. One example of a suitable powering component is discussed in U.S. Pat. No. 10,144,707 to Russo, et al, incorporated by reference in its entirety. Other known methods for powering implanted devices can also be used.

As seen in FIG. 1, the system 100 also includes a database 140. The database 140 stores a collection of images. Each image is associated in the database with a neural emission signature pattern, also stored in database 140.

A neural emission signature is a pattern reflecting a neural emission emitted by a person's brain in response to the stimulus of the associated image. In embodiments, a neural emission signature is created by showing a user a control image depicting a scene or an object (or a plurality of control images depicting the same scene or object). A sensor (which can be the same detecting electronics component 110 implanted within the user) detects the neural emissions in response to the user seeing the control image(s). The patterns associated with these neural emissions are then saved by the system 100 in the database 140 as the neural emission signature for that image (i.e., the scene or object depicted in the image) and an association between the neural emission signature and the image is created in the database 140. Thus, in these embodiments, the neural emission signatures are reflective of the user's actual reaction to seeing the objects in the control images.

In other embodiments, the neural emission detected can be one in reaction to a stimulus that can be, but is not required to be, visual. For example, it can be a neural emission can be in response to a smell, or a particular sound, or in recalling a traumatic memory. These neural emissions signatures are then associated by the system 100 to images that are therapeutic or that help counter the effects of the stimulus on the person. For example, if a certain sound triggers an anxiety in a user, the neural emissions signature associated with that sound can be linked to a calming image that is displayed to the user to help the user manage the anxiety.

In embodiments of the inventive subject matter, the system 100 also includes a camera that is implantable in the eye of the user. In these embodiments, the camera can be used to capture images that are used to create neural emission signatures for new objects/scenes.

The images stored by the database that are used in the systems and methods of the inventive subject matter can be one or more of still images, photographs, videos, or computer-generated images.

In embodiments, the images can be partially or entirely alphanumeric characters. For example, the image can be the name of a person displayed to the user when the user thinks about the person.

Figure 2:
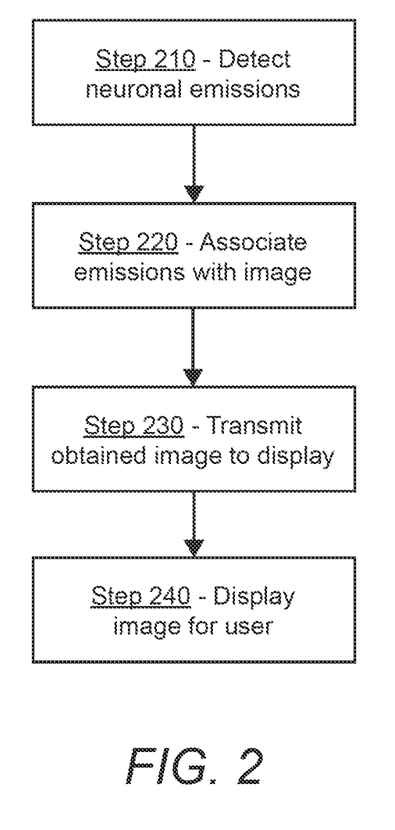
FIG. 2 is a flowchart illustrating a process according to embodiments of the inventive subject matter.

FIG. 2 provides an illustrative example of the processes according to embodiments of the inventive subject matter.

At step 210, the detecting electronics component 110 detects neuronal emissions from the user and transmits the neural emissions signals to the analytics electronic component 120. It should be appreciated that the detecting electronics component 110 can, in embodiments, be continuously detecting neuronal emissions and transmitting those to the analytics component 120. As such, the detecting electronics component 110 can transmit discrete, separate transmissions of neural emissions signals and/or continuous streams of neural emissions signals to the analytics electronic component 120.

At step 220, the analytics electronic component 120 receives the neural emissions signals and associates the neural emission signals with an image. The process of step 220 is illustrated in greater detail in FIG. 3.

Figure 3:
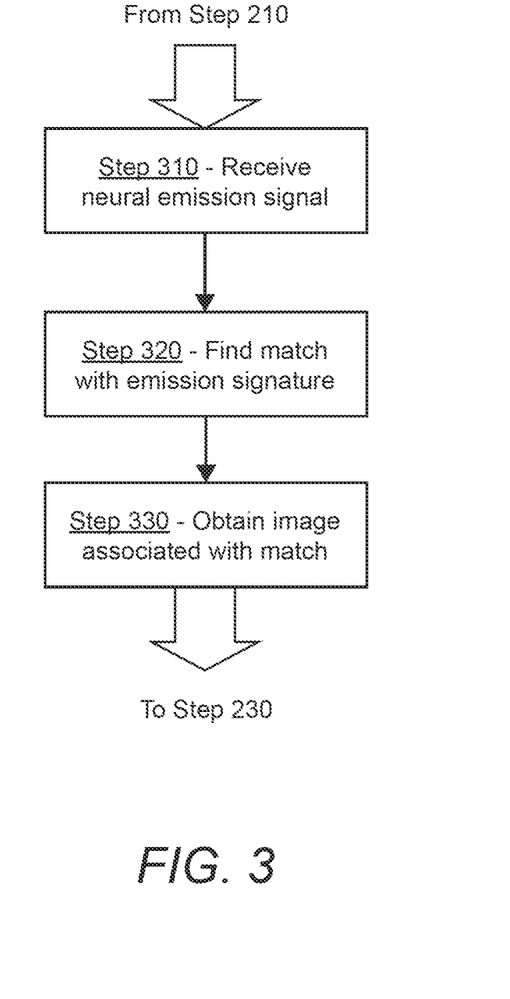
FIG. 3 is a flowchart illustrating the step of associating neural emission signals with an image in detail, according to embodiments of the inventive subject matter.

As seen in FIG. 3, the analytics electronic component 120 receives the neural emissions signals from the detecting electronics component 110 at step 310.

At step 320, the analytics electronics component 120 compares the received neural emissions signals to stored neural emission signature patterns to find a match.

Upon finding a match, the analytics electronics component 120 obtains an image associated with the matching neural emission signature pattern from the database at step 330.

The process then proceeds to step 230 of FIG. 2, where the analytics electronics component 120 transmits the obtained image to the display electronics component 130.

At step 240, the display electronics component 130 displays the image to the user. As discussed above, the display electronics component 130 is implanted inside the user's eye. As such, when the image is displayed to the user, only the user is able to see it.

In embodiments of the inventive subject matter, it is contemplated that multiple users can each have the corresponding components of the system 100 embedded and that these systems can communicate via wireless communication networks to exchange data.

Figure 4:
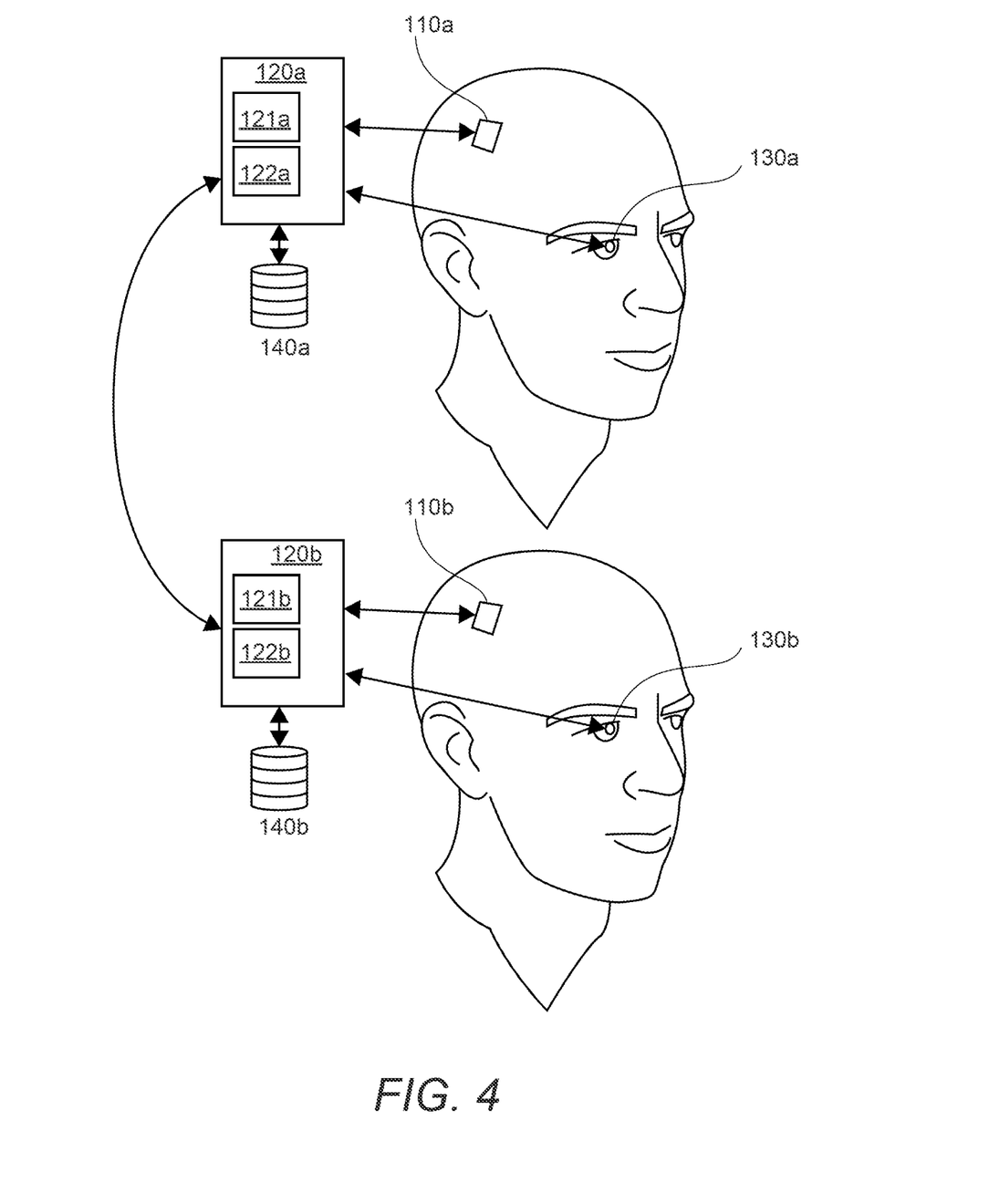
FIG. 4 provides a diagrammatic view of a multi-user environment, according to embodiments of the inventive subject matter.

An example of these embodiments is illustrated in FIG. 4. In these embodiments, a detecting electronics component 110a and analytics component 120a of a first user perform their respective steps 210 and 220 discussed above.

Then, the analytics component 120a transmits the obtained image to the analytics component 120b associated with a second user. The analytics component 120b then transmits the image to a corresponding display electronics component 130b implanted in the second user which proceeds to display the image such that the second user can see it. In these embodiments, the transmission of the image to the second analytics component 120b can be in addition to or instead of the transmission of the image to the display electronics component 130a of the first user for display to the first user.

The example embodiment of FIG. 4 essentially enables two users to communicate what they are thinking about without speaking or otherwise acting.

In a variation of these embodiments, a user can designate certain images associated with their neural emissions signature patterns as being excluded from sending. Thus, in these embodiments, the analytics component 130a checks whether the obtained image is designated as a "send protected" image prior to transmitting it to the analytics component 130b. If the image has been designated as a send protected image, the analytics component 130a does not transmit it. If the image has not been designated as a send protected image, the analytics component 130b proceeds to transmit it to the analytics component 130b. This way, a user is protected against sending potentially embarrassing or sensitive images (which might also disclose embarrassing or sensitive thoughts or feelings) to another user.

In embodiments, the analytics electronics component 120 is programmed to delay the presentation of the image to the user via the display electronics component 130 based on a condition or trigger. For example, if the analytics electronics component 120 determines that the user is sleeping, the analytics electronics component 120 will delay presentation of the image to the user until the user is awake. In embodiments, the analytics electronics component 120 can determine whether the user is asleep or awake based on an implanted camera within the eye. In these embodiments, if the images received from the camera are black (because the user's eye is closed) for a predetermined amount of time (e.g., over a minute, over 10 minutes, etc.), the analytics electronics component 120 determines the user is asleep. In another embodiment, the determination can be made based on the movement of the user (e.g., via an accelerometer or other movement detector implanted or worn by the user). If the accelerometer does not transmit signals for a predetermined amount of time, it is indicative that the user is at rest (and presumably asleep) and as such the analytics electronics component 120 determines that the user is asleep. In another embodiment, the analytics electronics component 120 can be programmed to delay the presentation of the image based on the time of day indicated by a system clock (e.g., 10:00 PM through 8:00 AM).

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A visualization system for visualizing neuronal activity of a person, comprising:
a detecting electronics component, positioned within an eye of the person, and configured to detect neuronal emissions of a person;
an analytic electronics component programmed to associate the neuronal emissions with an image; and
a display implantable within the eye of the person, the display configured to render at least a portion of the associated image.

2. The visualization system of claim 1, wherein the detecting electronics component is configured to receive neuronal emissions from a brain of a person.

3. The visualization system of claim 2, wherein the detecting electronics component is positioned subdermally in the head of the person.

4. The visualization system of claim 1, wherein a second detecting electronics component, configured to detect additional neuronal emissions of a person, is positioned over a portion of the spine of a person.

5. The visualization system of claim 1, wherein a second detecting electronics component, configured to detect additional neuronal emissions of a person, is positioned over a portion of the peripheral nervous system of a person.

6. The visualization system of claim 1, wherein the analytic electronics component is positioned within the eye of the person.

7. The visualization system of claim 1, wherein the image comprises a moving image.

8. The visualization system of claim 1, further comprising a camera implantable in the eye of the person, wherein the camera is configured to provide the image to the analytic electronics.

9. The visualization system of claim 1, further comprising:
the analytic electronics component programmed to transmit the image to a second analytic electronic component, wherein:
the second analytic electronics component is associated with a second person and communicatively coupled with a second display; and
the second display is implanted within an eye of the second person; and
the second display is configured to display the image to the second person.

10. The visualization system of claim 1, wherein the detecting electronics component and the display are integral to the same device.

\* \* \* \* \*